United States Patent [19]
Alder et al.

[11] Patent Number: 6,143,570
[45] Date of Patent: Nov. 7, 2000

[54] OPTICAL SENSOR FOR THE DETERMINATION OF IONS

[75] Inventors: Alex Alder, Arisdorf, Switzerland; Steven Barnard, Wellesley, Mass.; Joseph Berger, Basel, Switzerland

[73] Assignee: Novartis Corporation, Summit, N.J.

[21] Appl. No.: 09/307,914

[22] Filed: May 10, 1999

Related U.S. Application Data

[63] Continuation of application No. 08/704,703, filed as application No. PCT/IB95/00159, Mar. 13, 1995, abandoned.

[30] Foreign Application Priority Data

Mar. 25, 1994 [CH] Switzerland .......................... 917/94-0

[51] Int. Cl.$^7$ .................................................. G01N 21/64
[52] U.S. Cl. .............................. 436/74; 436/79; 436/172; 422/82.08; 422/57
[58] Field of Search .................. 422/82.08, 57; 436/73, 74, 79, 172

[56] References Cited

U.S. PATENT DOCUMENTS

| | | | |
|---|---|---|---|
| 4,549,951 | 10/1985 | Knudson et al. | 204/416 |
| 4,645,744 | 2/1987 | Charlton et al. | 436/74 |
| 4,762,799 | 8/1988 | Seitz et al. | |
| 5,354,825 | 10/1994 | Klainer et al. | 526/268 |
| 5,405,975 | 4/1995 | Kuhn et al. | 549/397 |
| 5,837,446 | 11/1998 | Cozzette et al. | 435/6 |
| 5,837,454 | 11/1998 | Cozzette et al. | 435/6 |

FOREIGN PATENT DOCUMENTS

| | | |
|---|---|---|
| 2119840 | 9/1994 | Canada . |
| 0207392a3 | 1/1987 | European Pat. Off. . |
| 0484865 | 5/1992 | European Pat. Off. . |
| 0582836 | 2/1994 | European Pat. Off. . |
| 0623599 | 11/1994 | European Pat. Off. . |
| 9117432 | 11/1991 | WIPO . |
| 9210739 | 6/1992 | WIPO . |

OTHER PUBLICATIONS

Analytical Chemistry, vol. 62, pp. 2054–2055 (1990).
Chem. Abstract 72:122891Y.
Chemical, Biochemical and Environmental Fiber Sensors II, vol. 1368, pp. 165–174 (1990).
He, H. et al. Novel type of ion–selective fluorosensor based on the inner filter effect: an optrode for potassium, Anal. Chem., vol. 65, pp. 123–127, (1993).
Journal of Fluorescence, vol. 2(2), pp. 93–97 (Jun. 1992).
Morf et al., Pure & Appl. Chem., vol. 61, pp. 1613–1618 (1989).
Roe et al., Analyst, vol. 115, pp. 353–358 (1990).
The Analyst, vol. 113(5), pp. 693–697 (May 1988).
Wang et al., Analytical Science, vol. 6, pp. 715–720 (1990).

Primary Examiner—Jeffrey Snay
Attorney, Agent, or Firm—Wenderoth, Lind & Ponack, L.L.P.

[57] ABSTRACT

A composition comprising
(a) a transparent support
(b) which is coated on at least one side with a transparent coating which comprises
  (b1) a plasticizer-free, hydrophobic polymer having a glass transition temperature Tg of from −150 to 50° C.,
  (b2) counterions in the form of lipophilic salts,
  (b3) an ionophore which forms a complex with the ion to be determined, and
  (b4) a compound of the formula I or II as fluorophore

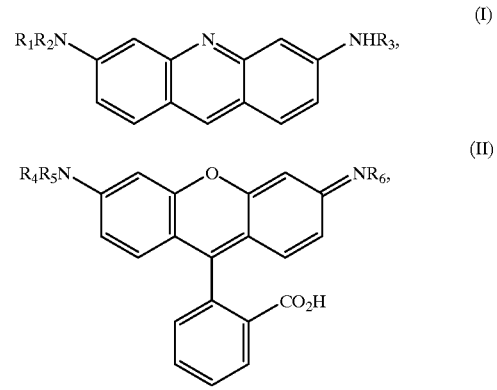

in which $R_1$ and $R_3$, and $R_4$ and $R_6$ are $C_1$–$C_{30}$alkyl or $C_1$–$C_{30}$alkyl-CO—, and $R_2$ and $R_5$ are H or $C_1$–$C_{30}$alkyl, with the proviso that the total number of carbon atoms in the alkyl groups is at least 5, or a salt thereof with an inorganic or organic acid. The composition is highly suitable for the qualitative or quantitative optical determination of ions by fluorescence detection.

43 Claims, No Drawings

OPTICAL SENSOR FOR THE DETERMINATION OF IONS

This application is a continuation of U.S. application Ser. No. 08/704,703, filed Nov. 15, 1996, now abandoned, the entire contents of which are incorporated herein by reference, which was the National Stage of International Application No. PCT/IB95/00159, filed Mar. 13, 1995.

The invention relates to a sensor for the optical determination of ions, for example cations from the group consisting of metal and ammonium cations, or for example anions from the group consisting of anions of inorganic and organic acids, in aqueous samples by the fluorescence method, which sensor contains certain highly basic dyes from the group consisting of rhodamines and acridines as fluorophores in the active coating, to a process for the qualitative or quantitative determination of cations, in particular in aqueous solutions, using the optical sensor, and to a composition containing the fluorophores and polymers.

The optical determination of ions has recently achieved increased importance, the presence or concentration of ions being measured, for example, via the change in absorption or fluorescence of a suitable dye. The sensors, also known as optrodes, generally comprise a transparent support material and an active coating. This active coating generally contains a transparent hydrophobic polymer and a lipophilic plasticizer for achieving adequate ion diffusion and solubility of the active constituents. The active constituents are a specific ionophore as complexing agent for ions, a counterion for maintaining electrical neutrality, and an indicator substance which, due to a chemical change or a physical change in the environment, generates a measurable optical signal.

U.S. Pat. No. 4,645,744 describes systems of this type in which the indicator substance is a neutral compound, for example a dye (p-nitrophenol), which interacts with an ionophore/metal cation complex, causing a colour change as the optically measurable signal. The interaction can cause, for example, the elimination of a proton from the dye, causing a change in the electron state. Suitable compounds include fluorescing compounds (for example fluorescein), whose fluorescence changes due to the change in the electron state and can be determined optically by means of fluorescence measurements.

H. He et al. in Chemical, Biochemical and Environmental Fiber Sensors II, SPIE Vol. 1368, pages 165 to 174 (1990), describe systems containing a proton carrier (Nile Blue) as indicator substance, in which the transport of potassium into the active coating by means of valinomycin as ionophore causes dissociation of the proton carrier and diffusion of a proton into the aqueous phase. The proton carrier changes its colour from blue to red and, depending on the choice of wavelength, either the reduction in fluorescence of the blue dye or the corresponding increase in the fluorescence of the red dye can be determined. Due to the higher sensitivity and selectivity, measurement of the fluorescence is preferred. A significant disadvantage of the process is the low sensitivity of the system, due to the low fluorescence quantum yield of the indicator dye used.

J. N. Roe in Analyst, Vol. 115, pages 353 to 358 (1990), describes a system based on energy transfer due to complex formation of the fluorescence dye used with the anionic form of a certain indonaphthol, which itself forms a ternary complex with the potassium-charged ionophore. The potassium is determined by measuring the change in absorption after charging with potassium or from the change in fluorescence. The sensitivity and response speeds of this system are regarded as unsatisfactory.

Y. Kawabata in Anal. Chem. Vol. 62, pages 1528–1531 and 2054 to 2055, describes a membrane system for the optical determination of potassium using a hydrophobic ion exchanger, namely 3,6-bis(dimethylamino)-10-dodecyl- or -10-hexadecylacridinium bromide. A change in fluorescence is achieved by changing the polarity in the microenvironment of the sample, since the acridinium salts diffuse at the interface with the aqueous phase due to ion exchange with the potassium ion.

W. E. Morf et al. in Pure & Appl. Chem., Vol. 61, No. 9, pages 1613 to 1618 (1989), describe the use of pH-sensitive chromo- or fluoroionophores for the optical determination of cations based on ion exchange reactions. The sensitivity of these systems is relatively low, the measurement is hindered in optically dense systems, and relatively high concentrations of chromo- or fluoroionophores in the membrane are required.

K. Wang et al. in Analytical Science, Vol. 6, pages 715 to 720 (1990), describe membranes containing an absorption dye (Nile Blue) as indicator substance for the optical measurement of metal cations. The system is based on an ion exchange mechanism which reduces the absorption by protonation of the dye. The sensitivity of the system is regarded as too low.

Hitherto, no systems have been disclosed which have an ion exchange mechanism for the optical measurement of ions and are based on the determination of the change in fluorescence of a fluorophore and have high sensitivity, since the fluorescence quantum yields and basicities of the known pH-sensitive fluorophores are too low.

The systems disclosed hitherto contain high-molecular-weight, hydrophobic polymers in combination with a plasticizer in the active coating in order to ensure rapid response times and adequate sensitivities. In these membrane materials, the long-term stability and repeated use are considerably restricted, since the plasticizer and other low-molecular-weight constituents, for example ionophores or fluorophores, are washed out in the course of time. Furthermore, low-molecular-weight substances can penetrate into the membrane and render the sensor unusable.

It has now been found that certain acridine dyes and rhodamine dyes surprisingly satisfy these high requirements and are lipophilic, pH-sensitive and highly basic fluorophores which are highly suitable, in a neutral polymer membrane together with an ionophore and a counterion, for the determination of ions by the ion exchange mechanism and have a fluorescence which is highly dependent on the corresponding ion concentrations. These fluorophores are distinguished by a high fluorescence quantum yield, high basicity, a large difference between the fluorescence signals of the protonated and deprotonated forms, high lipophilicity, adequate photostability and suitable absorption and emission wavelengths. Highly sensitive systems for the optical determination of ions on the basis of fluorescence measurements can be provided. Furthermore, it has been found, surprisingly, that the service life and use frequency can be considerably increased, since plasticizer-free, hydrophobic polymers having a defined glass transition range can be employed as the polymers in the membrane.

The invention relates to a composition comprising
 (a) a transparent support
 (b) which is coated on at least one side with a transparent coating which comprises
  (b1) a plasticizer-free, hydrophobic polymer having a glass transition temperature Tg of from −150 to 50° C.,
  (b2) counterions in the form of lipophilic salts, (b3) an ionophore which forms a complex with the ion to be determined, and (b4) a compound of the formula I or II as fluorophore

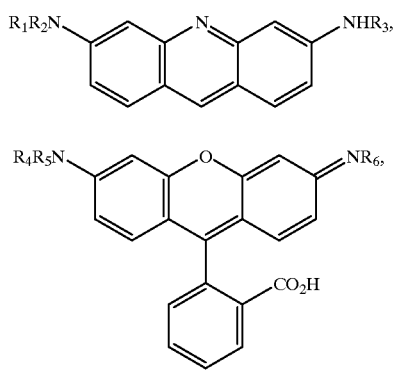

in which $R_1$ and $R_3$, and $R_4$ and $R_6$ are $C_1$–$C_{30}$alkyl or $C_1$–$C_{30}$alkyl-CO—, and $R_2$ and $R_5$ are H or $C_1$–$C_{30}$alkyl, with the proviso that the total number of carbon atoms in the alkyl groups is at least 5, and salts thereof with inorganic or organic acids.

The total number of carbon atoms in the alkyl groups is preferably at least 8, particularly preferably at least 10, especially preferably at least 12.

In a preferred embodiment, $R_2$ is H.

The alkyl groups can be linear or branched and preferably contain 1 to 22 carbon atoms. Linear alkyl groups are preferred. Examples of alkyl are methyl, ethyl and the isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl and tricontyl. In a preferred embodiment, $R_1$ and $R_3$ are $C_6$–$C_{24}$alkyl or $C_6$–$C_{24}$alkyl-CO—, particularly preferably $C_{10}$–$C_{24}$alkyl or $C_{10}$–$C_{24}$alkyl-CO—, especially preferably $C_{14}$–$C_{22}$alkyl or $C_{14}$–$C_{22}$alkyl-CO—, while $R_2$ is H. In another embodiment, $R_5$ is preferably H, and $R_4$ and $R_6$ are preferably $C_6$–$C_{24}$alkyl, particularly preferably $C_{10}$–$C_{24}$alkyl, especially preferably $C_{14}$–$C_{22}$alkyl. In a further embodiment, $R_4$ and $R_5$ are preferably $C_1$–$C_6$alkyl, particularly preferably $C_1$–$C_4$alkyl, especially preferably methyl or ethyl, and $R_6$ is $C_{10}$–$C_{24}$alkyl or $C_{10}$–$C_{24}$alkyl-CO—, preferably $C_{14}$–$C_{22}$alkyl or $C_{14}$–$C_{22}$alkyl-CO—, especially preferably $C_{16}$–$C_{22}$alkyl or $C_{16}$–$C_{22}$alkyl-CO—.

The salts of the compounds of the formulae I and II can be derived, for example, from HF, HCl, HBr, HI, $H_2SO_3$, $H_2SO_4$, $H_3PO_3$, $H_3PO_4$, $HNO_2$, $HNO_3$, $HClO_4$, $HBF_4$, $HB(C_6H_5)_4$, $HPF_6$, $HSbF_6$, $CF_3SO_3H$, toluenesulfonic acid, $C_1$–$C_4$alkyl- or phenylphosphonic acid, formic acid, acetic acid, propionic acid, benzoic acid, mono-, di- or trichloroacetic acid, or mono-, di- or trifluoroacetic acid. Preference is given to HCl, HBr, $H_2SO_4$, $HClO_4$, $HBF_4$, $HB(C_6H_5)_4$, $HPF_6$ and $HSbF_6$.

The compounds of the formulae I and II are novel and can be prepared in a manner known per se from commercial 3,6-diaminoacridine by stepwise alkylation by means of various alkylating agents or alkylation using one alkylating agent or acylating agent. Examples of suitable alkylating agents are dialkyl sulfates or monohaloalkanes, in particular chloro-, bromo- and iodoalkanes. Examples of suitable acylating agents are carboxylic anhydrides and in particular carboxylic acid halides, for example carboxylic acid chlorides. This reaction can be carried out in the presence of inert polar and aprotic solvents, for example ethers, alkylated acid amides and lactams or sulfones, and at elevated temperatures, for example from 50 to 150° C. It is expedient to add a hydrogen halide scavenger, for example alkali metal carbonates or tertiary amines, in particular sterically hindered tertiary amines.

The compounds of the formula II can be obtained, for example, by reacting phthalic anhydride with 2 mol equivalents of 3-monoalkylaminophenol. Another possible preparation comprises reacting 3-monoalkylaminophenol with 1 mol equivalent of 2-hydroxy-4-dialkylamino-2'-carboxybenzophenone. These reactions are described, for example, in U.S. Pat. No. 4,622,400. The reaction is expediently carried out in an inert solvent, for example hydrocarbons or ethers. Molar amounts of a condensation agent, for example Lewis acids, concentrated sulfuric acid, perchloric acid or phosphoric acid, are advantageously added. The reaction temperatures can be, for example, from 50 to 250° C.

The compounds of the formula I can be isolated in a conventional manner by precipitation, crystallization or extraction and purified, if necessary, by recrystallization or chromatography. They are crystalline, red, red-brown or red-violet compounds.

The compounds of the formulae I and II are highly suitable as fluorophoric dye indicators for the optical determination of ions in an aqueous environment, in particular by measurement of the change in fluorescence.

The compounds of the formulae I and II preferably have a $pK_a$ value of at least 8, particularly preferably at least 10.

The support can be formed, for example, from a plastic material, for example polycarbonate or acrylic sheeting, mineral materials or glass and can have any desired shape, for example plates, cylinders, tubes, tapes or fibres. Glasses are preferred.

The thickness of the coating on the support can be, for example, from 0.01 to 100 μm, preferably from 0.1 to 50 μm, more preferably from 0.1 to 30 μm, and particularly preferably from 0.1 to 10 μm.

Various types of hydrophobic polymer are suitable for the composition, where the term hydrophobic indicates that the water content in the polymers is at most 15% by weight, preferably at most 10% by weight, particularly preferably at most 5% by weight, especially preferably at most 3% by weight, based on the polymer. They expediently have a mean molecular weight of at least 5 000, preferably at least 10 000 and particularly preferably at least 20 000 daltons, for example from 20 000 to 200 000 daltons, preferably from 50 000 to 200 000 daltons. The polymers must have adequate solubility in organic solvents so that they can be mixed with the other components and can be converted into coatings by conventional coating methods. They must furthermore be permeable to ions. The glass transition temperature is preferably from −130 to 0° C. The dielectric constant of the polymers is preferably from 2 to 25, particularly preferably from 5 to 15, at 100 Hz and room temperature. The optical transparency is preferably in the range from 400 to 1200 nm, particularly preferably from 400 to 900 nm.

Suitable polymers are known to the person skilled in the art. They can be homopolymers, copolymers, block polymers, graft polymers and polymer alloys. The components of a polymer alloy may be a combination of two or more polymer components, said components having high and low glass transition temperatures. The glass transition temperature can be adjusted, for example, by means of the polarity and the chain length and content of structural units. The polymers can be selected, for example, from the group consisting of polyolefins, polyesters, polyamides, polyethers, polyimides, polyesteramides, polyamideimides, polyurethanes, polyetherurethanes, polyesterurethanes, polyureas, polyurethaneureas and polysiloxanes, it being possible for the polymers to contain ionizable, basic groups (for example amino groups) or ionizable, acidic groups (for example carboxyl or sulfonyl groups), which may be used as replacement for a counterion of lipophilic salts and can provide improved ion transport.

Some examples of monomers for the preparation of polyolefins are $C_2$–$C_{12}$olefins, acrylic acid, methacrylic acid, maleic acid, maleic anhydride, $C_1$–$C_{30}$ esters of acrylic and methacrylic acid, $C_1$–$C_{30}$ amides of acrylic and methacrylic acid, acrylamide and methacrylamide, vinyl esters of $C_1$–$C_{20}$carboxylic acids, acrylonitrile, butadiene, isoprene, chlorobutadiene, styrene, α-methylstyrene, vinyl chloride, vinyl fluoride, vinylidene chloride and vinyl ethers of $C_1$–$C_{30}$alcohols.

Polyesters, polyesteramides and polyamides are preferably synthesized from $C_2$–$C_{12}$dicarboxylic acids and $C_2$–$C_{18}$diols or -diamines. Polyimides are preferably synthesized from $C_2$–$C_{18}$tetracarboxylic acids and $C_2$–$C_{18}$diamines. Polyethers are preferably synthesized from aliphatic $C_2$–$C_{12}$diols (1,2- or α,ω-lining) or linear adducts of these diols and $C_8$–$C_{30}$diglycidyl ethers. Polyurethanes and polyureas are preferably synthesized from $C_2$–$C_{18}$diols or -diamines and $C_2$–$C_{20}$diisocyanates and/or triisocyanates. Polysiloxanes are preferably synthesized from di($C_1$–$C_4$)alkylsilyldichlorosilanes.

In a preferred embodiment, the hydrophobic polymers are polyurethanes made from polyethers of $C_3$–$C_6$alkanediols and aliphatic, cycloaliphatic, cycloaliphatic-aliphatic, aromatic-aliphatic or aromatic $C_2$–$C_{20}$diisocyanates, for example from polytetrahydrofuran and bis(p-diisocyanatocyclohexyl)methane (Tecoflex®).

In another preferred embodiment, the hydrophobic polymers are copolymers comprising
a) from 10 to 90 mol %, preferably from 20 to 80 mol %, particularly preferably from 30 to 70 mol %, of identical or different structural units of the formula III

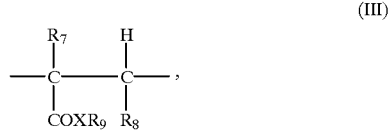

(III)

and from 90 to 10 mol %, preferably from 80 to 20 mol %, particularly preferably from 70 to 30 mol %, based on the polymer, of identical or different structural units of the formula IV,

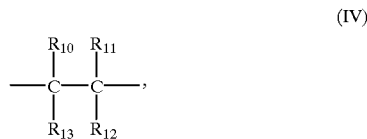

(IV)

in which $R_7$ and $R_8$, independently of one another, are H or $C_1$–$C_4$alkyl, X is —O— or —$NR_{14}$—, $R_9$ is $C_6$–$C_{20}$alkyl and $R_{14}$ is H or $C_1$–$C_{20}$alkyl; $R_{10}$ and $R_{11}$, independently of one another, are H, F, Cl or $C_1$–$C_4$alkyl, $R_{12}$ and $R_{13}$, independently of one another, are H, F, Cl, $C_1$–$C_4$alkyl, —COOH, —COO—$C_1$–$C_5$alkyl, —CONH$C_1$–$C_5$alkyl or —CON($R_{14}$)$C_1$–$C_5$alkyl, or $R_{12}$ is H and $R_{13}$ is —CN, phenyl, chlorophenyl, $C_1$–$C_{12}$alkoxy or $C_2$–$C_{18}$acyloxy.

$R_7$ is preferably H or methyl, and $R_8$ is preferably H. X is preferably —O—. $R_9$ is preferably $C_6$–$C_{18}$alkyl. Examples of $R_9$ are hexyl, heptyl, octyl, 2-ethylhexyl, nonyl, decyl, dodecyl, tetradecyl, hexadecyl and octadecyl.

$R_{10}$ is preferably H or methyl, $R_{11}$ is preferably H, and $R_{12}$ is preferably H. $R_{13}$ is preferably —CN, phenyl, —COO—$C_1$–$C_4$alkyl, $C_1$–$C_4$alkoxy or $C_2$–$C_6$acyloxy. Some examples of acyloxy are acetyloxy, propionyloxy, butyroyloxy, pentanoyloxy and hexanoyloxy.

Examples of suitable salts with lipophilic anions are alkali metal, alkaline earth metal and ammonium salts with substituted or unsubstituted tetraphenylborates. Preferred cations are $Li^{\oplus}$, $Na^{\oplus}$, $K^{\oplus}$, $Mg^{2\oplus}$, $Ca^{2\oplus}$, $NH_4^{\oplus}$, and the ammonium cations of primary, secondary and tertiary amines and quaternary ammonium cations which can contain from 1 to 60 carbon atoms. Some examples of ammonium cations are methyl-, ethyl-, propyl-, butyl-, hexyl-, octyl-, decyl-, dodecyl-, tetradecyl-, hexadecyl-, octadecyl-, dimethyl-, diethyl-, dibutyl-, butylmethyl-, dioctyl-, didoceyl-, dodecylmethyl-, trimethyl-, triethyl-, tripropyl-, tributyl-, trioctyl-, tridodecyl-, dodecyldimethyl-, didodecylmethyl-, tetramethyl-, tetraethyl-, tetrapropyl-, tetrabutyl-, tetrahexyl-, tetraoctyl-, tetradecyl-, tetradodecyl-, dodecyltrimethyl-, octyltrimethyl-, didodecyldimethyl-, tridodecylmethyl-, tetradecyltrimethyl- and octadecyltrimethylammonium. Quaternary ammonium salts are preferred, in particular those having 4 to 48, preferably 4 to 24, carbon atoms. Other suitable salts with lipophilic anions are alkali metal, alkaline earth metal and ammonium salts of anionic surfactants, for example of $C_{12}$–$C_{22}$fatty acids or $C_{12}$–$C_{22}$alkylsulfonic acids, $C_{12}$–$C_{22}$alkylphosphates, $C_4$–$C_{18}$alkylbenzoic acids, $C_4$–$C_{18}$alkylphenylsulfonic acids or $C_4$–$C_{18}$alkylphenylphosphonic acids.

An example of a suitable borate anion is tetraphenylborate, whose phenyl groups may be substituted by one or more, preferably 1 to 3, particularly preferably 1 or 2, $C_1$–$C_4$alkyl, $C_1$–$C_4$alkoxy, halogen, for example F or Cl, or trifluoromethyl groups. Some specific examples are tetraphenylborate, tetra(3,5-bistrifluoromethylphenyl)borate and tetra(4-chlorophenyl)borate. The salts with lipophilic anions serve as negative charge compensation for the metal cations diffusing into the active coating and to be measured therein in complexed form.

The salts with lipophilic anions can also be salts of polymers containing acidic or basic groups, for example polysulfonic acids or polycarboxylic acids. These polymers can also be structural units (randomly distributed structural units or block elements) of the hydrophobic polymers.

The amount of salts with lipophilic anions can be, for example, from 0.01 to 10% by weight, preferably from 0.1 to 5% by weight, particularly preferably from 0.1 to 2% by weight, based on the amount of polymer.

The polymer coating (also referred to as membrane) contains an ionophore in, for example, an amount of from 0.01 to 10% by weight, preferably from 0.1 to 5% by weight, particularly preferably from 0.1 to 2% by weight, based on the amount of polymer. Ionophores are natural or synthetic organic compounds which contain a plurality of, usually alternating, electron-rich heteroatoms, for example S, N and in particular O, in linear or cyclic carbon chains and which are capable of selectively complexing the ions to be measured. The natural compounds are frequently macrocyclic compounds, for example valinomycin, which is capable of selectively binding potassium cations. Another example is nonactin. A large group of ionophores comprises macrocyclic polyethers (crown ethers), which are capable of complexing various metal cations, depending on the geometry and size. Further examples of ionophores are coronandenes, kryptandenes and calixarenes. Examples of open-chain ionophores are podandenes. Such ionophores are described, for example, in U.S. Pat. No. 4,645,744.

Examples of ionophores for anions are open-chain or macrocyclic polyamines (mono- and polycyclic compounds, usually in protonated form as polycations or as quaternary (poly)ammonium salts); open-chain or macrocyclic (mono- and polycyclic) polyamides; open-chain or macrocyclic (cyclic) polypyridinium compounds; calixarenes; cyclodextrins; cobyrinates and metal porphyrin complexes; open-chain or macrocyclic metallocene compounds; mono- and polydentate ligand systems containing, for example, B, Si, Al or Sn as complexing ligand atoms.

The amount of compounds of the formulae I and II can be, for example, from 0.01 to 10% by weight, preferably from 0.1 to 5% by weight, particularly preferably from 0.1 to 2% by weight, based on the amount of polymer.

The fluorophores to be used according to the invention have very suitable absorption and emission wavelength ranges which allow the use of known and inexpensive light sources, for example halogen or xenon lamps or light-emitting diodes. Examples of detectors which can be employed are photodiodes. The fluorophores furthermore have high absorption coefficients and high quantum yields can be achieved. The high lipophilicity, high basicity and the large dynamic range of the change in fluorescence between the protonated and deprotonated forms satisfy, in particular, the high requirements for optical determination of ions based on fluorescence measurements. Both cations and anions can be determined.

Examples of suitable cations are cations of metals from the first to fifth main groups and the first to eighth sub-groups of the Periodic Table of the Elements, the lanthanides and actinides. Some examples of metals are Li, Na, K, Rb, Cs, Mg, Ca, Sr, Ba, B, Al, Ga, In, Tl, Sn, Pb, Sb, Bi, Cu, Ag, Au, Zn, Cd, Hg, Sc, Y, Ti, Zr, Hf, Cr, Mo, W, Mn, Fe, Co, Ni, Ru, Os, Rh, Ir, Pt, Pd, La, Ce, Pr, Nd, Pm, Sm, Eu, Gd, Th, Dy, Ho, Er, Yb, Lu, Ac, Th, Pa, U, Np and Pu. Preferred cations are the alkali and alkaline earth metal ions, in particular $Li^{\oplus}$, $Na^{\oplus}$, $K^{\oplus}$, $Mg^{2\oplus}$, $Ca^{2\oplus}$ and $Sr^{2\oplus}$, very particularly $K^{\oplus}$, $Na^{\oplus}$ and $Ca^{\oplus}$. Examples of suitable ammonium cations are $NH_4^{\oplus}$ and the cations of protonated primary, secondary and tertiary amines and quaternary ammonium. The amines can contain from 1 to 40, preferably from 1 to 20, particularly preferably from 1 to 12, carbon atoms. The quaternary ammonium can contain from 4 to 40, preferably from 4 to 20, particularly preferably from 4 to 16, carbon atoms.

The anions to be measured can be derived from mineral acids, oxygen acids and inorganic complex acids. Examples are the halides and pseudohalides $F^{\ominus}$, $Cl^{\ominus}$, $Br^{\ominus}$, $I^{\ominus}$, $N_3^{\ominus}$, $CN^{\ominus}$, $OCN^{\ominus}$ and $SCN^{\ominus}$; anions of inorganic oxygen acids $NO_2^{\ominus}$, $NO_3^{\ominus}$, $CO_3^{\ominus}$, $PO_4^{3\ominus}$, $SO_4^{2\ominus}$, $ClO_4^{\ominus}$, $MnO_4^{\ominus}$ and $ClO_3^{\ominus}$; anions of inorganic complex acids $Fe(CN)_6^{4\ominus}$ and $Co(CN)_6^{3\ominus}$; anions of carboxylic acids, phenols and nucleotide anions, such as adenosine phosphate.

The composition according to the invention is highly suitable as an optical sensor for the quantitative determination of ions, in particular cations, very particularly metal cations, for example potassium cations, in an aqueous environment, preferably by means of fluorescence spectrometry. The determinations can be carried out quickly with high accuracy even for low concentrations (for example in the micromolar range to the nanomolar range), since the pH-dependent equilibria of the complexing reactions and of proton exchange become established quickly and the fluorophores are characterized by a high fluorescence quantum yield and sensitivity. The analyses can be carried out, for example, directly in body fluids (blood, urine, serum), natural water or waste water, where it may be possible for any interfering cations to be specifically bound or removed in advance. The composition according to the invention is particularly suitable for the determination of physiological amounts, for example for potassium in the range from 0.5 to 10 mmol, of cations in aqueous media. By means of the anionic compounds of the formula II, which generally have pK values of below 6, this property of fluorophore can be used for the determination of anions, particularly halides, especially chloride, by the novel detection method, since a pK range of below 6 and, for example, up to about 4 is favourable for this detection.

In addition to the preferred method of fluorescence spectroscopy, other optical measurement methods may also be used, for example surface plasmoresonance spectroscopy, absorption spectroscopy, reflection spectroscopy, interferometry or surface-amplified Raman or fluorescence spectroscopy.

The invention furthermore relates to a composition comprising (a) a plasticizer-free, hydrophobic polymer having a glass transition temperature Tg of from −150 to 50° C. and (b) a compound of the formula I or II as fluorophore

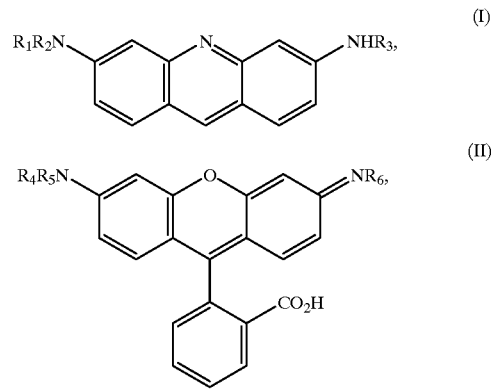

in which $R_1$ and $R_3$, and $R_4$ and $R_6$ are $C_1$–$C_{30}$alkyl or $C_1$–$C_{30}$alkyl-CO—, and $R_2$ and $R_5$ are H or $C_1$–$C_{30}$alkyl, with the proviso that the total number of carbon atoms in the alkyl groups is at least 5, or salts thereof with inorganic or organic acids, (c) an ionophore which forms a complex with the ion to be determined, and (d) counterions in the form of lipophilic salts.

The abovementioned preferences and embodiments apply to this composition. The composition has a long shelf life and is a coating composition for the production of sensors.

The novel composition may additionally comprise inert solvents, where the concentration of the composition in the solution is from 1 to 50% by weight, preferably from 5 to 40% by weight, particularly preferably from 5 to 30% by weight, based on the solution.

Examples of suitable inert solvents are protic-polar and aprotic solvents, which can be used alone or in mixtures of at least two solvents. Examples are: ethers (dibutyl ether, tetrahydrofuran, dioxane, ethylene glycol monomethyl and dimethyl ether, ethylene glycol monoethyl and diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1, 2,2-tetrachloroethane), carboxylates and lactones (ethyl acetate, methyl propionate, ethyl benzoate, 2-methoxyethyl acetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine), aliphatic and aromatic hydrocarbons, for example petroleum ether, pentane, hexane, cyclohexane, methylcyclohexane, benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile). The choice of a solvent depends essentially on the solubility of the individual components in the novel composition, which, as a coating for a sensor, should give a highly homogeneous mixture. Preferred solvents are aprotic polar solvents.

The invention furthermore relates to an optical sensor for the determination of cations in aqueous measurement samples, in particular by means of fluorescence spectrometry, which comprises (a) a transparent support, (b) which is coated on at least one side with a transparent coating comprising (b1) a plasticizer-free, hydrophobic polymer having a glass transition temperature of from −150 to 50° C., (b2) a counterion in the form of a salt of a lipophilic anion, (b3) an ionophore which forms a complex with the ion to be determined, and (b4) a compound of the formula I or II as the fluorophore.

The abovementioned preferences and embodiments apply to the sensor.

The novel sensor is produced by coating the support. Conventional processes, for example brushing, knife coating, dipping, spraying, pouring, curtain coating and spin coating, can be used for this purpose. In order to improve adhesion, the support can be provided, before the coating, with adhesion-promoting layers, for example by treatment with alkyl chlorosilanes.

The invention furthermore relates to a method for the optical determination of ions in aqueous measurement samples, in which a composition according to the invention is brought into contact with said aqueous measurement sample, and then, in particular, the change in fluorescence of the fluorophore in the active polymer coating is measured.

The process according to the invention can be carried out, for example, by immobilizing the composition according to the invention comprising support and active polymer coating in an optical cell in which the active coating is brought into contact with the measurement sample. The optical cell contains a window through which the active coating can be excited by irradiation and the emitted fluorescence radiation can be measured by means of a spectrofluorometer. The wavelengths are adjusted so that the absorption is at a maximum for the irradiation and the emission is at a maximum for the fluorescence measurement. The intensity is measured as a function of time. The measurement system can be designed so that the measurement is carried out discontinuously or continuously, for example by pumping the measurement solution through the measurement cell. In order to determine unknown concentrations of cations, the system can first be calibrated by means of measurement samples of known concentration, and the concentrations are plotted as a function of the fluorescence intensity. It is expedient to add pH buffers to the measurement sample, since the sensitivity of the measurement, and consequently also the fluorescence intensity of the fluorophore, depends on the pH of the measurement solution due to the pH-dependence of the absorption spectrum. In another embodiment, this pH-dependency can, however, also be determined and taken into account in the calculation. The pH range of the measurement sample can be, for example, from 4 to 8, more preferably from 6.5 to 7.5. Examples of suitable buffers are citrate buffers and phosphate buffers. Further buffer systems are described in U.S. Pat. No. 4,645,744, in particular including those which are incorporated directly into the active coating in order to avoid addition to the measurement sample.

The examples below illustrate the invention in greater detail.

A) Preparation of fluorophores of the formulae I and II

EXAMPLE A1

Preparation of 3,6-bis(n-octylamino)acridine 6.33 g of anhydrous potassium carbonate are added to a solution of 2.5 g of 3,6-diaminoacridine hydrochloride and 3.55 ml of 1-bromooctane in 50 ml of dimethyl sulfoxide, and the mixture is stirred at 80° C. for 48 hours. The cooled reaction mixture is subsequently poured onto ice, and the brown suspension is extracted with methylene chloride. The organic phase is washed with saturated aqueous NaCl solution and dried over sodium sulfate. After evaporation, the red-brown oil is chromatographed on silica gel using methylene chloride/methanol (9:1). After evaporation of the solvent, the residue is taken up in diethyl ether/methanol (10:1) and chromatographed on aluminium oxide. The eluate is taken up in methanol, 2N HCl is added, the mixture is extracted with diethyl ether, and the ether phase is dried and evaporated. The residue is dissolved in methylene chloride, n-hexane is added, and the red crystalline precipitate formed is filtered off. Further product can be isolated from the mother liquor after evaporation. The melting point of the title compound is 245° C. Absorption spectrum (ethanol): $\lambda_{max}$=472 nm; $\epsilon$=51 400.

EXAMPLE A2

Preparation of 3,6-bis(n-eicosylamino)acridine 2.53 g of anhydrous potassium carbonate are added to a solution of 2.5 g of 3,6-diaminoacridine hydrochloride and 2.95 g of 1-eicosyl bromide in 20 ml of N,N'-dimethylethyleneurea, and the mixture is stirred at 50° C. for 86 hours. The cooled reaction mixture is subsequently poured into water, and the orange-brown suspension is extracted with methylene chloride. The organic phase is washed with water and dried over sodium sulfate. After evaporation, 2N HCl is added to the brown oil. The red precipitate formed is filtered off, washed with water and then dried in a high vacuum. The resultant red-brown crystals are taken up in methylene chloride/methanol (10:1) and chromatographed on silica gel. After evaporation, the residue is taken up in diethyl ether/methanol (10:1) and re-chromatographed on silica gel, giving the title compound as red crystals, absorption spectrum (ethanol): $\lambda_{max}$=472 nm; $\epsilon$=42 200.

EXAMPLE A3

Preparation of 3,6-bis(n-hexylamino)acridine 298 mg of ground potassium hydroxide are added to a solution of 500 mg of N,N'-bistosyl-3,6-diaminoacridine and 797 mg of 1-bromohexane in 25 ml of dimethylformamide, and the mixture is stirred at 60° C. for 22 hours. The cooled reaction mixture is subsequently poured into water and extracted with ethyl acetate, and the organic phase is separated off, washed with aqueous NaCl solution and then dried over sodium sulfate. Evaporation gives a dark-red oil, which is taken up in toluene/ethyl acetate (20:1) and chromatographed on silica gel. Evaporation of the solvent gives a yellow, viscous oil, which is dissolved in 11.5 ml of glacial acetic acid, 4.6 ml of 97% sulfuric acid are added with water cooling, and the mixture is then stirred at room temperature for 15 hours. The red reaction mixture is poured into ice water and adjusted to pH 11 by means of 30% NaOH. The mixture is extracted with ethyl acetate, and the organic phase is washed with 2N HCl and saturated aqueous NaCl solution and then dried over sodium sulfate. After evaporation, the dark-red, viscous oil is taken up in t-butyl methyl ether/methanol (5:1) and chromatographed on silica gel, giving the title compound as orange-red crystals having a melting point of >200° C. (decomposition). $^1$H-NMR (CDCl$_3$): 8.1 [s, 1H, C(9)]; 7.44 [d, 2H, C(8)]; 6.93 [s, 2H, C(S)]; 6.82 [d, 2H, C(7)]; 3.20 [t, 4H, N-CH$_2$]; 1.68 [m, 6H, CH$_3$].

EXAMPLE A4

Preparation of 3,6-bis(n-heptylcarbonylamino) acridine 3.1 ml of heptanoyl chloride are slowly added dropwise to a suspension of 2.5 g of 3,6-diaminoacridine hydrochloride in 50 ml of pyridine, and the mixture is then stirred for 30 minutes. The reaction mixture is subsequently poured into water. The yellow suspension is extracted with methylene chloride, and the organic phase is washed with aqueous saturated NaCl solution and dried over sodium sulfate. After evaporation, the dark-red oil is taken up in methylene chloride/methanol (10:1) and chromatographed on silica gel. The evaporated eluate is taken up in methylene chloride and added dropwise to cyclohexane. The yellow precipitate formed is filtered off, washed with cyclohexane and dried in a high vacuum, giving the title compound as yellow crystals having a melting point of 243–244° C. Absorption spectrum (ethanol): $\lambda_{max}$=384 nm; $\epsilon$=2 300.

EXAMPLE A5

Preparation of

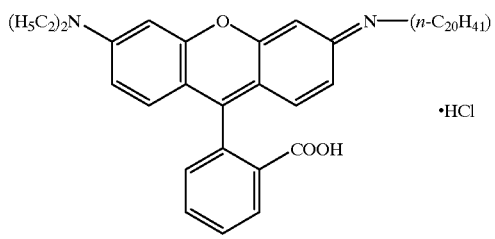

a) A solution of 12.8 g of phthalic anhydride and 13.2 g of 3-N,N-diethylaminophenol is stirred at 110° C. for 16 hours in 75 ml of toluene. The precipitated product is filtered off and recrystallized from ethanol, giving brick-red crystals of 1-carboxy-1'-hydroxy-3'-diethylaminobenzophenone (product A) having a melting point of 214° C.

b) A solution of 5.5 g of 3-aminophenol and 21.6 g of 1-bromoeicosane in 250 ml of 1,4-dioxane is stirred at 100° C. for 48 hours. The mixture is evaporated in vacuo, and the brown, gelatinous residue is taken up in toluene/ethyl acetate (10:1) and chromatographed on silica gel, giving 3-N-eicosylaminophenol as white crystals having a melting point of 80° C.

c) 626 mg of product A and 790 mg of 3-N-eicosylaminophenol are stirred for 2 hours at 170° C. in 5 ml of phosphoric acid (85%). After cooling, a solution of 1 ml of concentrated HCl in 1 ml of methanol is added, and the mixture is subsequently extracted with methylene chloride. After removal of the solvent, the residue is taken up in methylene chloride/methanol (85:15) and chromatographed on silica gel, giving the title compound as red-violet crystals having a melting point of 115° C. Absorption spectrum (ethanol): $\lambda_{max}$=532 nm; $\epsilon$=90 000.

EXAMPLE A6

Preparation of

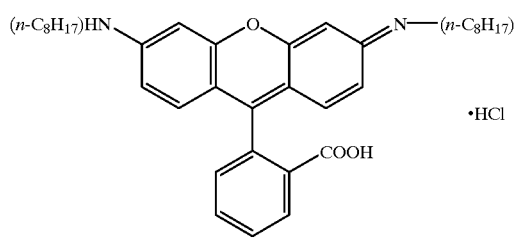

a) A solution of 5.45 g of 3-aminophenol and 11.6 g of 1-bromooctane in 250 ml of dioxane is stirred at 100° C. for 80 hours, the solvent is then evaporated, and the residue is then taken up in toluene/ethyl acetate (10:1) and chromatographed on silica gel, giving N-octylaminophenol as beige crystals, melting point 75° C.

b) 1.1 g of N-octylaminophenol and 0.37 g of phthalic anhydride are melted together at 100° C. 1 ml of phosphoric acid (85%) is added to the melt, which is then heated to 170° C. After 1 hour, the mixture is allowed to cool and 2N HCl is added. The mixture is extracted with methylene chloride, the solvent is removed, and the red residue is taken up in methylene chloride/methanol (85:15). Chromatography on silica gel gives the title compound as red crystals having a melting point of 183° C. Absorption spectrum (ethanol): $\lambda_{max}$=522 nm; $\epsilon$=73 700.

EXAMPLE A7

Preparation of

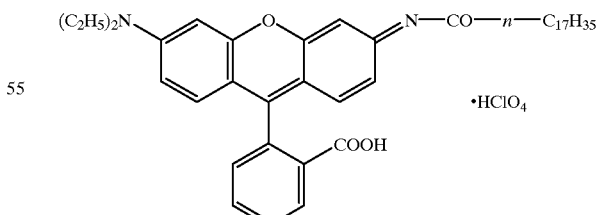

a) 1.57 g of product A from Example A5a, 0.55 g of 3-aminophenol and 10 ml of phosphoric acid (85%) are stirred for 30 minutes at 170° C. 6.7 ml of perchloric acid (50%) and 100 ml of methanol are then added, the mixture is re-heated, and the solvent is then removed in vacuo. The residue is taken up in methylene chloride, the solution is washed with water, and the solvent is removed again. The residue is taken up in methylene chloride/methanol (10:1) and chromatographed on silica gel, giving red crystals of compound B of the formula

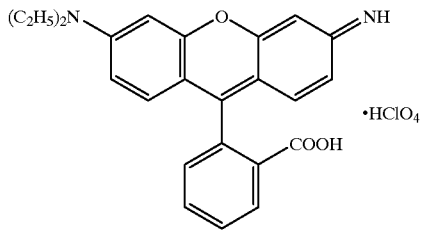

having a melting point of 175° C.

b) 0.1 g of compound B is dissolved in 1 ml of methylene chloride and 0.3 ml of pyridine, and 100 mg of stearoyl chloride are added. After 3 hours, the mixture is evaporated to dryness in vacuo, and the residue is dissolved in methylene chloride/methanol (85:15) and chromatographed on silica gel, giving the title compound as red crystals having a melting point of 145° C. Absorption spectrum (ethanol): $\lambda_{max}$=560 nm; $\epsilon$=10 900.

B) Preparation of polymers

EXAMPLES B1 TO B7

The monomers listed in Table 1 are introduced into an ampoule in the stated mixing ratios together with 0.1% by weight of α,α'-azobisisobutyronitrile. In order to remove oxygen, the ampoule is evacuated and filled with nitrogen a number of times, then sealed, warmed to 60° C. and left at this temperature for 48 hours. The mixture is then cooled and dissolved in ten times the amount (based on the monomers) of tetrahydrofuran (THF). This solution is transferred into 20 times the amount of methanol, and the precipitated polymer is then filtered off. The dried polymer is re-dissolved in THF and precipitated using methanol, separated off and then dried in vacuo for 48 hours.

In Table 1 below, the following abbreviations are used: AN=acrylonitrile, DodMA=dodecyl methacrylate, EHA= ethylhexyl acrylate, MMA=methyl methacrylate, VAC= vinyl acetate. The inherent viscosity (IV) is determined at 25° C. in a solution of 0.5% by weight of polymer in THF.

TABLE 1

| Example No. | DodMA (mol %) | AN (mol %) | VAC (mol %) | EHA (mol %) | MMA (mol %) | Yield (% by wt.) | IV (dl/g) |
|---|---|---|---|---|---|---|---|
| B1 | 50 | 25 | 25 | — | — | 76 | 1.765 |
| B2 | 60 | 20 | 20 | — | — | 50 | 0.229 |
| B3 | 40 | 12 | 48 | — | — | 66 | 1.075 |
| B4 | 40 | 6 | 54 | — | — | 52 | 1.092 |
| B5 | 40 | 40 | — | — | 20 | 87 | 2.560 |
| B6 | — | 40 | 20 | 40 | — | 90 | 1.386 |

EXAMPLES B6 AND B7

The procedure is as in Examples B1–B6, using ethyl acetate (EA), acrylonitrile (AN) and ethylhexyl acrylate (EHA). The results are shown in Table 2.

TABLE 2

| Example No. | EA (mol %) | AN (mol %) | EHA (mol %) | Yield (% by wt.) | IV (dl/g) |
|---|---|---|---|---|---|
| B7 | 90 | 10 | — | 54 | 1.394 |
| B8 | — | 10 | 90 | 82 | 0.663 |

C) Production of coated supports

EXAMPLES C1–C8 a) Support material

The support material used is pretreated glass. Circular glass sheets (diameter 18 mm, thickness 0.17 mm) are immersed for one hour in a solution of 10% by volume of dimethyldodecylchlorosilane in isopropanol. The glass sheets are then each washed one after the other with 200 ml of isopropanol, ethanol and methanol and dried at 110° C. for 1 hour. The hydrophobicized surface has better adhesion of the membrane coating.

b) Preparation of the coating solution.

The following constituents are introduced into a 2 ml bottle together with tetrahydrofuran (THF) and shaken until the components have dissolved. The fluorophore used is the compound of Example A5.

EXAMPLE C1

125 mg of polymer from Example B1, 1.0 mg of fluorophore, 1.5 mg of valinomycin, 1.2 mg of potassium tetrakis[3,5-(trifluoromethyl)phenyl]borate, 3 ml of THF.

EXAMPLE C2

100 mg of polymer from Example B2, 1.0 mg of fluorophore, 1.5 mg of valinomycin, 1.2 mg of potassium tetrakis[3,5-(trifluoromethyl)phenyl]borate, 2 ml of THF.

EXAMPLE C3

40 mg of polymer from Example B3, 1.5 mg of fluorophore, 1.5 mg of valinomycin, 1.2 mg of potassium tetrakis[3,5-(trifluoromethyl)phenyl]borate, 2 ml of THF.

EXAMPLE C4

38 mg of polymer from Example B4, 1.5 mg of fluorophore, 1.5 mg of valinomycin, 1.2 mg of potassium tetrakis[3,5-(trifluoromethyl)phenyl]borate, 2 ml of THF.

EXAMPLE C5

50 mg of polymer from Example B7, 1.5 mg of fluorophore, 1.5 mg of valinomycin, 1.2 mg of potassium tetrakis[3,5-(trifluoromethyl)phenyl]borate, 2 ml of THF.

EXAMPLE C6

20 mg of polyurethane Tecoflex® (Thermedics Inc., Woburn) having a Tg of −70° C., 0.5 mg of fluorophore, 0.24 mg of valinomycin, 0.2 mg of potassium tetrakis[3,5-(trifluoromethyl)phenyl]borate, 1 ml of THF.

EXAMPLE C7

100 mg of polyurethane Tecoflex® (Thermedics Inc., Woburn) having a Tg of −70° C., 3 mg of fluorophore, 50 mg of diethyl N,N-[(4R,5R)-4,5-dimethyl-1,8-dioxo-3,6-dioxaoctamethylene)bis(12-methylamino)dodecanoate (calcium ionophore, Fluka 21102), 6 mg of potassium tetrakis[3,5-(trifuoromethyl)phenyl]borate, 2 ml of THF.

c) Production of coated glass supports.

The glass supports are clamped in the chamber of a spin-coating apparatus (Optocoat OS 35var, Willer Company, CH-8484 Weisslingen). The chamber is rinsed with 10 ml of tetrahydrofuran and rotated for 2 minutes at 3 800 revolutions/minute. 50 μl of the particular coating solution are then pipetted onto the glass support, and the glass support is rotated for a further 10 seconds. The glass support coated with a membrane is then removed and dried for 10 minutes in air.

D) Determination of ion concentrations

EXAMPLES D1 TO D6

The coated glass supports are clamped in an optical cell in which the membrane is in contact with the measurement liquid. The membrane can be optically excited in the optical cell and the fluorescence radiation measured. The optical cell is introduced into a spectrofluorometer (Perkin-Elmer LS-50). The absorption and emission wavelengths are adjusted to the corresponding maxima of the fluorophores employed in the membrane. The membrane is brought into contact with an aqueous KCl solution or $CaCl_2$ solution of defined concentration by pumping the solution through the cell at a rate of 1 ml/min and determining the change in fluorescence intensity. Before the measurement and after each measurement, the cell is rinsed with potassium ion-free buffer solutions and the fluorescence intensity is determined in order to define the base line. The fluorescence intensity (measured as the change in voltage in the photodiode) in percent at the respective potassium concentration for the fluorophore of Example A5 (membrane B1) and various compositions as in Examples C1–C7 is shown in the tables below.

Example D1 (membrane C2):

| Potassium concentration (mM) | Fluorescence (volts) |
|---|---|
| 0.00 | 4.32 |
| 0.1 | 3.96 |
| 0.5 | 3.67 |
| 1.0 | 3.52 |
| 3.0 | 3.46 |
| 5.0 | 3.33 |
| 7.0 | 3.23 |
| 10.0 | 3.15 |

Example D2 (membrane C6):

| Potassium concentration (mM) | Fluorescence (volts) |
|---|---|
| 0.00 | 5.30 |
| 0.1 | 3.20 |
| 0.5 | 1.70 |
| 1.0 | 1.20 |
| 3.0 | 0.50 |
| 5.0 | 0.40 |
| 7.0 | 0.30 |
| 10.0 | 0.20 |

Example D3 (membrane C1):

| Potassium concentration (mM) | Fluorescence (volts) |
|---|---|
| 0.00 | 6.89 |
| 0.5 | 4.00 |
| 4.0 | 2.89 |
| 10.0 | 1.89 |

Example D4 (membrane C4):

| Potassium concentration (mM) | Fluorescence (volts) |
|---|---|
| 0.00 | 6.80 |
| 0.5 | 4.50 |
| 4.0 | 3.20 |
| 10.0 | 2.50 |

Example D5 (membrane C5):

| Potassium Concentration (mM) | Fluorescence (volts) |
|---|---|
| 0.00 | 3.00 |
| 0.5 | 2.40 |
| 4.0 | 2.25 |
| 10.0 | 2.15 |

Example D6 (membrane C7):

| Potassium concentration (mM) | Fluorescence (volts) |
|---|---|
| 0.00 | 1.55 |
| 0.1 | 0.96 |
| 0.5 | 0.75 |
| 1.0 | 0.65 |
| 3.0 | 0.50 |
| 5.0 | 0.45 |
| 7.0 | 0.40 |
| 10.0 | 0.38 |

What is claimed is:

1. A composition comprising
    (a) a transparent support
    (b) which is coated on at least one side with a transparent coating which comprises
        (b1) a plasticizer-free, hydrophobic polymer having a glass transition temperature $T_g$ of from −150 to 50° C.,
        (b2) counterions in the form of lipophilic salts,
        (b3) an ionophore which forms a complex with the ion to be determined, and
        (b4) a compound of the formula I or II as fluorophore

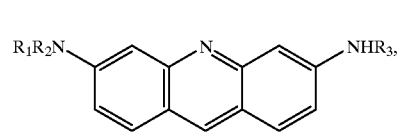

(I)

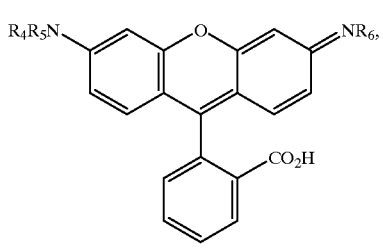

(II)

in which $R_1$ and $R_3$, and $R_4$ and $R_6$ are $C_1$–$C_{30}$ alkyl or $C_1$–$C_{30}$alkyl-CO—, and $R_2$ and $R_5$ are H or $C_1$–$C_{30}$alkyl, with the proviso that the total number of carbon atoms in the alkyl groups is at least 5, or a salt thereof with an inorganic or organic acid, wherein components (b1) to (b4) are not covalently bonded to one another.

2. A composition according to claim 1, wherein $R_2$ is H.

3. A composition according to claim 1, wherein the alkyl groups are linear alkyl groups.

4. A composition according to claim 1, wherein the alkyl groups contain 1 to 22 carbon atoms.

5. A composition according to claim 1, wherein $R_1$ and $R_3$ are $C_6$–$C_{24}$alkyl or $C_6$–$C_{24}$alkyl-CO—, and $R_2$ is H.

6. A composition according to claim 5, wherein $R_1$ and $R_3$ are $C_{10}$–$C_{24}$alkyl or $C_{10}$–$C_{24}$alkyl-CO—.

7. A composition according to claim 5, wherein $R_1$ and $R_3$ are $C_{14}$–$C_{22}$alkyl or $C_{14}$–$C_{22}$alkyl-CO—.

8. A composition according to claim 1, wherein $R_5$ is H and $R_4$ and $R_6$ are $C_6$–$C_{24}$alkyl.

9. A composition according to claim 8, wherein $R_4$ and $R_6$ are $C_{10}$–$C_{24}$alkyl.

10. A composition according to claim 9, wherein $R_4$ and $R_6$ are $C_{14}$–$C_{22}$alkyl.

11. A composition according to claim 1, wherein $R_4$ and $R_5$ are $C_1$–$C_6$alkyl, and $R_6$ is $C_{10}$–$C_{24}$alkyl or $C_{10}$–$C_{22}$alkyl-CO—.

12. A composition according to claim 11, wherein $R_4$ and $R_5$ are $C_1$–$C_4$alkyl, and $R_6$ is $C_{14}$–$C_{22}$alkyl or $C_{14}$–$C_{22}$alkyl-CO—.

13. A composition according to claim 12, wherein $R_4$ and $R_5$ are methyl or ethyl, and $R_6$ is $C_{16}$–$C_{22}$alkyl or $C_{16}$–$C_{22}$alkyl-CO—.

14. A composition according to claim 1, wherein the salt of the compound of the formula I or II is derived from HF, HCl, HBr, HI, $H_2SO_3$, $H_2SO_4$, $H_3PO_3$, $H_3PO_4$, $HNO_2$, $HNO_3$, $HClO_4$, $HBF_4$, $HPF_6$, $HSbF_6$, $CF_3SO_3H$, $HB[C_6H_5]_4$, toluenesulfonic acid, $C_1$–$C_4$alkyl- or phenylphosphonic acid, formic acid, acetic acid, propionic acid, benzoic acid, mono-, di- or trichloroacetic acid, or mono-, di- or trifluoroacetic acid.

15. A composition according to claim 14, wherein the salt of the compound of the formula I or II is derived from HCl, HBr, $H_2SO_4$, $HClO_4$, $HBP_4$, $HPF_6$, $HB[C_6H_5]_4$ or $HSbF_6$.

16. A composition according to claim 1, wherein the compound of the formula I or II has a $pK_a$ value of at least 8.

17. A composition according to claim 16, wherein the $pK_a$ value is at least 10.

18. A composition according to claim 1, wherein the support is a glass.

19. A composition according to claim 1, wherein the thickness of the coating on the support is from 0.01 to 100 μm.

20. A composition according to claim 1, wherein the hydrophobic polymer has a molecular weight of at least 5 000 daltons.

21. A composition according to claim 1, wherein the hydrophobic polymer is selected from the group consisting of the polyolefins, polyesters, polyamides, polyethers, polyimides, polyesteramides, polyamideimides, polyurethanes, polyetherurethanes, polyesterurethanes, polyureas, polyurethaneureas and polysiloxanes.

22. A composition according to claim 21, wherein the polymers contain ionizable basic or acidic groups.

23. A composition according to claim 21, wherein the hydrophobic polymers are polyurethanes made from polyethers of $C_3$–$C_6$alkanediols and aliphatic, cycloaliphatic, cycloaliphatic-aliphatic, aromatic-aliphatic or aromatic $C_2$–$C_{20}$diisocyanates.

24. A composition according to claim 21, wherein the hydrophobic polymers are copolymers comprising
a) from 10 to 90 mol % of identical or different structural units of the formula III

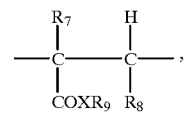

(III)

and from 90 to 10 mol % based on the polymer, of identical or different structural units of the formula IV,

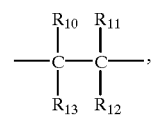

(IV)

in which $R_7$ and $R_8$, independently of one another, are H or $C_1$–$C_4$alkyl, X is —O— or —$NR_{14}$—, $R_9$ is $C_6$–$C_{20}$alkyl and $R_{14}$ is H or $C_1$–$C_{20}$alkyl; $R_{10}$ and $R_{11}$, independently of one another, are H, F, Cl or $C_1$–$C_4$alkyl, $R_{12}$ and $R_{13}$, independently of one another, are H, F, Cl, $C_1$–$C_4$alkyl, —COOH, —COO—$C_1$–$C_5$alkyl, —CONH$C_1$–$C_5$alkyl or —CON($R_{14}$)$C_1$–$C_5$alkyl, or $R_{12}$ is H and $R_{13}$ is —CN, phenyl, chlorophenyl, $C_1$–$C_{12}$alkoxy or $C_2$–$C_{18}$acyloxy.

25. A composition according to claim 1, wherein the salt with a lipophilic anion is an alkali metal, alkaline earth metal or ammonium salt with a substituted or unsubstituted tetraphenylborate.

26. A composition according to claim 25, wherein the cation is $Li^\oplus$, $Na_\oplus$, $K^\oplus$, $Mg^{2\oplus}$, $Ca^{2\oplus}$, $NH_4^\oplus$ or an ammonium cation of a primary, secondary or tertiary amine or a quaternary ammonium cation containing 1 to 40 carbon atoms.

27. A composition according to claim 25, wherein the borate anion is tetraphenylborate, whose phenyl groups are unsubstituted or substituted by one or more $C_1$–$C_4$alkyl, $C_1$–$C_4$alkoxy, halogen or trifluoromethyl groups.

28. A composition according to claim 25, wherein the borate anion is tetraphenylborate, tetra(3,5-bistrifluoromethylphenyl)borate or tetra(4-chlorophenyl)borate.

29. A composition according to claim 16, wherein the amount of the salt with a lipophilic anion is from 0.01 to 10% by weight, based on the amount of polymer.

30. A composition according to claim 1, wherein the polymer coating contains an ionophore in an amount of from 0.01 to 10% by weight, based on the amount of polymer.

31. A composition according to claim 1, wherein the potassium ionophore is valinomycin.

32. A composition according to claim 1, wherein the amount of the compound of the formula I or II is from 0.01 to 10% by weight, based on the amount of polymer.

33. A composition according to claim 32, wherein the amount of the compound of the formula I or II is from 0.1 to 5% by weight.

34. A composition according to claim 32, wherein the amount of the compound of the formula I or II is from 0.1 to 2% by weight.

35. A composition according to claim 1, wherein the total number of carbon atoms in the alkyl groups is at least 10.

36. A composition according to claim 1, wherein the total number of carbon atoms in the alkyl groups is at least 12.

37. The composition as claimed in claim 1, wherein the composition is formed by mixing the polymer, counterions, ionophore, and fluorophore together to form a coating, and applying the coating to the transparent support.

38. The composition as claimed in claim 37, wherein the polymer, counterions, ionophore, and fluorophore are mixed together in a single step.

39. A composition comprising
(a) a plasticizer-free, hydrophobic polymer having a glass transition temperature Tg of from −150 to 50° C., and
(b) a compound of the formula I or II as fluorophore

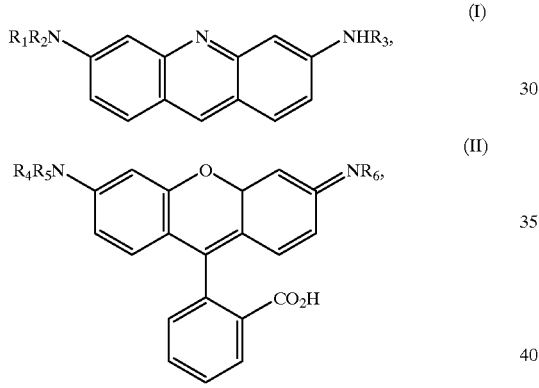

in which $R_1$ and $R_3$, and $R_4$ and $R_6$ are $C_1$–$C_{30}$ alkyl or $C_1$–$C_{30}$alkyl-CO—, and $R_2$ and $R_5$ are H or $C_1$–$C_{30}$alkyl, with the proviso that the total number of carbon atoms in the alkyl groups is at least 5, or a salt thereof with an inorganic or organic acid,
(c) an ionophore which forms a complex with the ion to be determined, and
(d) counterions in the form of lipophilic salts,
wherein components (a) to (d) are not covalently bonded to one another.

40. The composition as claimed in claim 39, wherein the composition is formed by mixing the polymer, counterions, ionophore, and fluorophore together.

41. The composition as claimed in claim 40, wherein the polymer, counterions, ionophore, and fluorophore are mixed together in a single step.

42. An optical sensor for the determination of ions in aqueous measurement samples, in particular by means of fluorescence spectrometry, which comprises (a) a transparent support
(b) which is coated on at least one side with a transparent coating which comprises
(b1) a plasticizer-free, hydrophobic polymer having a glass transition temperature $T_g$ of from −150 to 50° C.,
(b2) the salt of a lipophilic anion,
(b3) an ionophore which forms a complex with the ion to be determined, and
(b4) a compound of the formula I or II as fluorophore

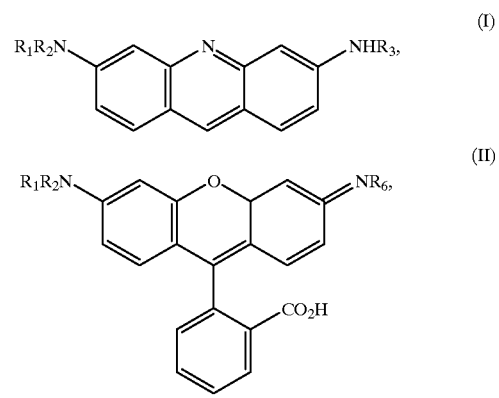

in which $R_1$ and $R_3$, and $R_4$ and $R_6$ are $C_1$–$C_{30}$ alkyl or $C_1$–$C_{30}$alkyl-CO—, and $R_2$ and $R_5$ are H or $C_1$–$C_{30}$alkyl, with the proviso that the total number of carbon atoms in the alkyl groups is at least 5, or a salt thereof with an inorganic or organic acid,
wherein components (b1) to (b4) are not covalently bonded to one another.

43. A method for the optical determination of ions in aqueous measurement samples, in which a sensor according to claim 42 is brought into contact with said aqueous measurement sample, and the change in fluorescence of the fluorophore in the active polymer coating is then measured.

* * * * *